United States Patent [19]

Greenstein et al.

[11] Patent Number: 5,224,680
[45] Date of Patent: Jul. 6, 1993

[54] SURGICAL INSTRUMENT HOLDER

[75] Inventors: Robert J. Greenstein, Tenafly, N.J.; Gregory Diamant, New York, N.Y.

[73] Assignee: Automated Medical Products Corp., New York, N.Y.

[21] Appl. No.: 748,705

[22] Filed: Aug. 22, 1991

[51] Int. Cl.⁵ .......................................... A61B 19/00
[52] U.S. Cl. ................... 248/316.4; 128/20; 248/316.6
[58] Field of Search ............ 248/316.6, 316.4, 231.6, 248/231.4, 229; 128/20

[56] References Cited

U.S. PATENT DOCUMENTS

| 1,074,272 | 9/1913 | Kline | 248/229 |
|---|---|---|---|
| 2,062,156 | 11/1936 | Zorbst | 248/229 X |
| 2,670,732 | 3/1954 | Nelson | 248/229 X |
| 2,814,455 | 11/1957 | Rainey | 248/316.6 X |
| 2,840,241 | 6/1958 | Callais | 248/231.4 |
| 3,237,899 | 3/1966 | Lewis | 248/316.6 X |
| 4,561,163 | 12/1985 | Cox | 248/316.4 X |
| 4,617,916 | 10/1986 | Le Vahn et al. | 128/20 |
| 4,867,404 | 9/1989 | Harrington et al. | 248/316.4 X |
| 4,919,379 | 4/1990 | Goetz | 248/231.6 |
| 4,958,793 | 9/1990 | Hess | 248/316.6 X |

FOREIGN PATENT DOCUMENTS 446439 3/1949 Italy ........................................ 128/20

Primary Examiner—David L. Talbott
Attorney, Agent, or Firm—Wigman, Cohen, Leitner & Myers

[57] ABSTRACT

A surgical instrument holder, adapted to be received and retained by an operating room table clamping apparatus is disclosed. The inventive holder is particularly suited for adjustably mounting and stabilizing a laparoscope, endoscope or similar instrument which has an elongated shaft. The holder comprises a clamping assembly mounted at one end of the holder for holding the shaft of the instrument. The clamping assembly includes a pair of movable jaws adapted for being closed about the shaft of the instrument. Means carried by another end of the holder for cooperating with the operating room table clamping apparatus are provided.

34 Claims, 3 Drawing Sheets

SURGICAL INSTRUMENT HOLDER

BACKGROUND OF THE INVENTION

1. Field Of The Invention

The present invention relates generally to improvements in devices for supporting laparoscopes or similar surgical instruments and more particularly to support devices which will adequately secure the instrument without causing damage thereto.

2. Description Of The Prior Art

To lessen the number of personnel needed for a surgical procedure, a variety of support apparatus exists for holding instruments in the desired position to perform the procedure. For example, U.S. Pat. Nos. 4,867,404 to Harrington et al. and 4,573,452 to Greenberg disclose flexible holders for cytoscopes and laparoscopes, respectively. Additionally, U.S. Pat. No. 373,362 to Hamilton, U.S. Pat. No. 2,070,670 to Marshall and U.S. Pat. No. 3,810,462 to Szpur disclose a variety of surgical instrument support devices. The Marshall patent describes a clamp for holding a retractor having a spring 18 located on a screw 13 intermediate clamp jaws 10, 11 urging the clamp jaws apart. A handle 17 operates screw 13 to move the jaws thereby tightening or releasing the retractor. Hamilton discloses a clamp N for holding a speculum P comprising a pair of jaws which open and close by means of a tightening screw o. Spzur discloses a clamp head 28 for holding a retractor blade 26. An open space 54 is defined intermediate jaws 30, 31 to permit the blade handle 48 to pivot (FIG. 6). By tightening handle 52, the retractor blade is fixed in any desired position.

There are a number of mechanical arm devices in commercial use, which are designed to be secured to operating room tables and which fix surgical instruments or clamps for use by the surgeon. Such devices generally include one or more pivotable arms at one end and at the free end a specialized clamp, socket, tool, or instrument is provided. One such mechanical arm is described in U.S. Pat. No. 4,143,652 to Meir et al and sold under the trademark IRON INTERN ® by Automated Medical Corporation of New York, N.Y. Other mechanical arms, e.g., "MARTIN ARM" are also commercially available.

Laparoscopy is a method for direct visualization of intra-abdominal organs. A laparoscope is an elongated viewing apparatus usually comprising glass fibers for transmission of light. A lens and/or television camera may be attached at the viewing end. The laparoscope is usually introduced into the abdomen via a trocar cannula. The trocar cannula disclosed in U.S. Pat. No. 4,654,030 to Moll et al. and sold under the trademark SURGIPORT ® Disposable Surgical Trocar by United States Surgical Corporation of Norwalk, Conn. is representative of the type of disposable trocar cannula which may be employed with the holder of the present invention.

It is frequently necessary to remove the viewing apparatus from the abdomen in order to clean or defog the lens. When the viewing apparatus is reinserted into the abdomen via the trocar cannula, it is desirable that the precise repositioning be achieved so that the organs being examined remain in view. Otherwise, valuable time is lost when surgical personnel must reposition the laparoscope.

To permit manipulation or operation within the abdomen, one or more additional trocar cannulae may be inserted into the abdomen for the introduction of various instruments such as probes, grasping forceps, cautery devices, and the like. See, U.S. Pat. No. 4,112,932 to Chiulli for a description of laparoscopy and a laparoscopic cannula.

Laparoscopes in use today usually comprise an elongated tubular metal member. These metal tubes are usually very thin and therefore easily bent or crimped. Such bending can interfere with the viewing quality, thereby rendering the instrument permanently inoperative. Many types of trocar cannulae are similarly constructed of a thin metal. If these cannulae are bent while being held this can interfere with the passage of instruments therethrough. Alternatively, these cannulae may be made of plastic. This is to permit x-rays to pass through them, thereby permitting operative cholesystography to be performed. This plastic has insufficient strength to permit grasping for fixing in one position without deformation.

A key disadvantage of the prior art devices is that they are not suitable for securely gripping sensitive surgical instruments such as a laparoscopes, trocar cannulae, and other instruments used during laparoscopic surgery. The prior art devices often damage the instruments by exerting a clamping force which causes the walls of the instrument to buckle or bend or which damages the insulation.

Another disadvantage of the prior art devices is the fact that they are complex, bulky, and comprise a large number of interconnected or linking elements. As a result, the prior art holders are susceptible to slippage and other inadvertent movement that also interfere with the work of the surgeons and other personnel. As will be appreciated, even the slightest unwarranted movement during these surgical procedures can result in dire consequences.

Yet another disadvantage of the prior art devices is the fact that they usually must engage the laparoscope or other instrument prior to the instrument being introduced into the abdomen via the trocar cannula. This limits the manipulability of the instrument for positioning and the like. U.S. Pat. No. 4,573,452 to Greenberg is an example of one such device having this disadvantage.

Still another disadvantage of the prior art clamping devices is that they are not compatible with existing mechanical arms which are mounted to operating room tables, for holding surgical instruments in place.

OBJECTS AND SUMMARY OF THE INVENTION

In view of the foregoing, it should be apparent that a need still exists in the art for a surgical instrument holder that avoids the problems inherent in the prior art devices. Accordingly, it is a primary object of this invention to provide a surgical instrument holder which can be used to secure a surgical and ancilliary delicate instrument without causing damage thereto, especially where the instrument shaft is made of metal, or metal coated with a plastic insulating layer to prevent unintended electrical shock to the patient or surgeon.

Another object of this invention is to provide a surgical instrument holder which is of sufficient rigidity to obviate slippage or inadvertent movement, without being intrusive.

Yet another object of this invention is to provide a surgical instrument holder for a laparoscope or the like which is especially adapted to fit the IRON IN- TERN® surgical retaining device as disclosed in the '652 patent to Meir et al.

Yet another object of this invention is to provide a surgical instrument holder capable of securely gripping a disposable trocar made of plastic without deforming the shaft so as to render it inoperative.

Yet another object of this invention is to provide a surgical instrument holder adaptable to grip the instrument after it has been introduced and positioned in the patient's body.

Briefly stated, the present invention is designed to grip and secure instruments, especially laparoscopes, used during surgery. For example, the laparoscope can be readily moved back and forth in the secured trocar to change the field of vision. The holder generally has two plates or jaws, which are screwed together to grip the instrument. A spring is disposed between the plates to push them apart when unscrewed. The present invention is applicable to, and removable from, any laparoscopic instrument at any stage during a laparoscopic surgical procedure. Specifically, the subject holder does not have to be positioned on an instrument prior to the instrument being passed through its introducing cannula.

In a first embodiment, the holder jaws are each provided with a longitudinal notch which cooperate to receive and grip a laparoscope or other operating instrument thereto. The recess formed by the cooperating notches allows the instrument to be held securely to avoid inadvertent extrusion or unwanted movement without causing damage to the instruments. The first embodiment is especially useful for holding laparoscopes having a metal shaft. This embodiment may also be used to grip a metal trocar cannula or the metal shaft of other instruments, such as probes, grasping forceps, and the like which are introduced through the trocar.

In a second embodiment for gripping the head of a disposable trocar made of plastic, each jaw is provided with a rough gripping surface and/or serrations instead of the longitudinal notch provided with the first embodiment. The second embodiment includes a safety provision which prevents the jaws from being approximated closer than 12 mm. This prevents accidental use with delicate and expensive instruments for which it was not intended to be used, such as an instrument having a metal or electrically insulated shaft.

With the foregoing and other advantages and features of the invention that will become hereinafter apparent, the nature of the invention may be more clearly understood by reference to the following detailed description of the invention, the appended claims and to the several views illustrated in the drawings.

BRIEF DESCRIPTION OF THE DRAWINGS

FIG. 4b is a longitudinal section of FIG. 4a;

FIG. 5b is an enlarged elevational view of an alternative embodiment of the surgical instrument of FIG. 5a.

DETAILED DESCRIPTION OF THE PREFERRED EMBODIMENTS

Figure 1:
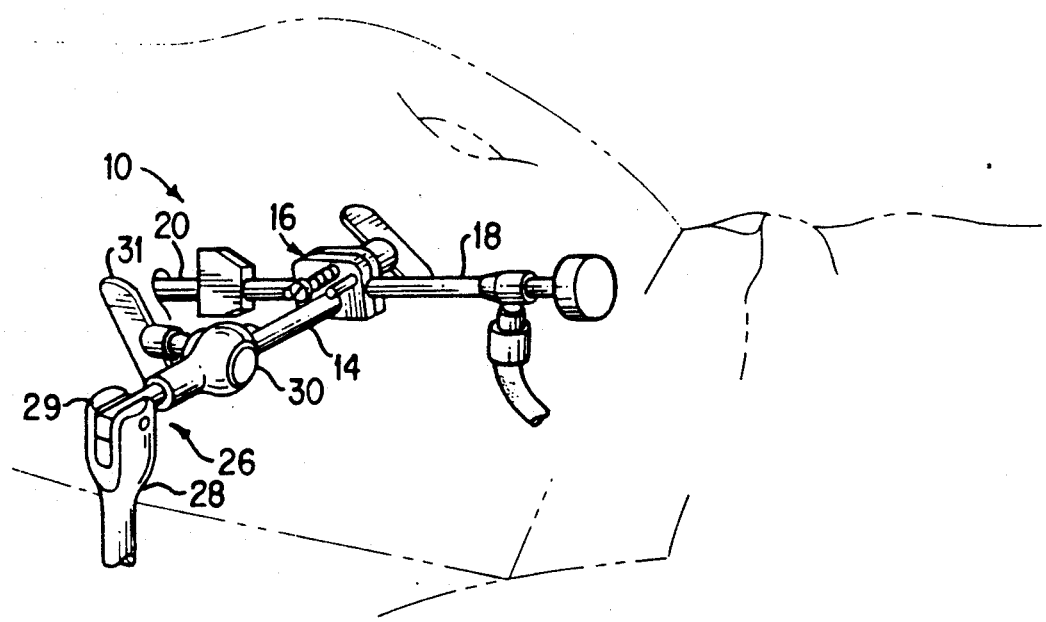
FIG. 1 is a perspective view of the surgical instrument holder of the present invention shown holding a laparoscope.

Referring now in detail to the drawings wherein like parts are designated by like reference numerals throughout, there is illustrated in FIGS. 1-4 the first embodiment of the surgical instrument holder of the present invention, designated generally by reference numeral 10.

Referring now to FIG. 1, holder 10 generally comprises an arm 14 and clamp assembly 16. The clamp assembly 16 is shown holding a typical laparoscope 18 which has been introduced into a patient's abdomen via a trocar cannula 20. Holder 10 may similarly be used to grip the cannula portion of the trocar 20 or any other instrument introduced through the trocar such as probes, grasping forceps, and the like. Arm 14 of holder 10 is removably attached to the IRON INTERN® operating room table clamping apparatus 26 described in the Meir et al patent. The IRON INTERN® comprises a plurality of elongated members 28 pivotably connected by means of joints 29, a socket 30 for receiving arm 14 and a threaded adjustment knob 31 to retain arm 14 therein.

Figure 2:
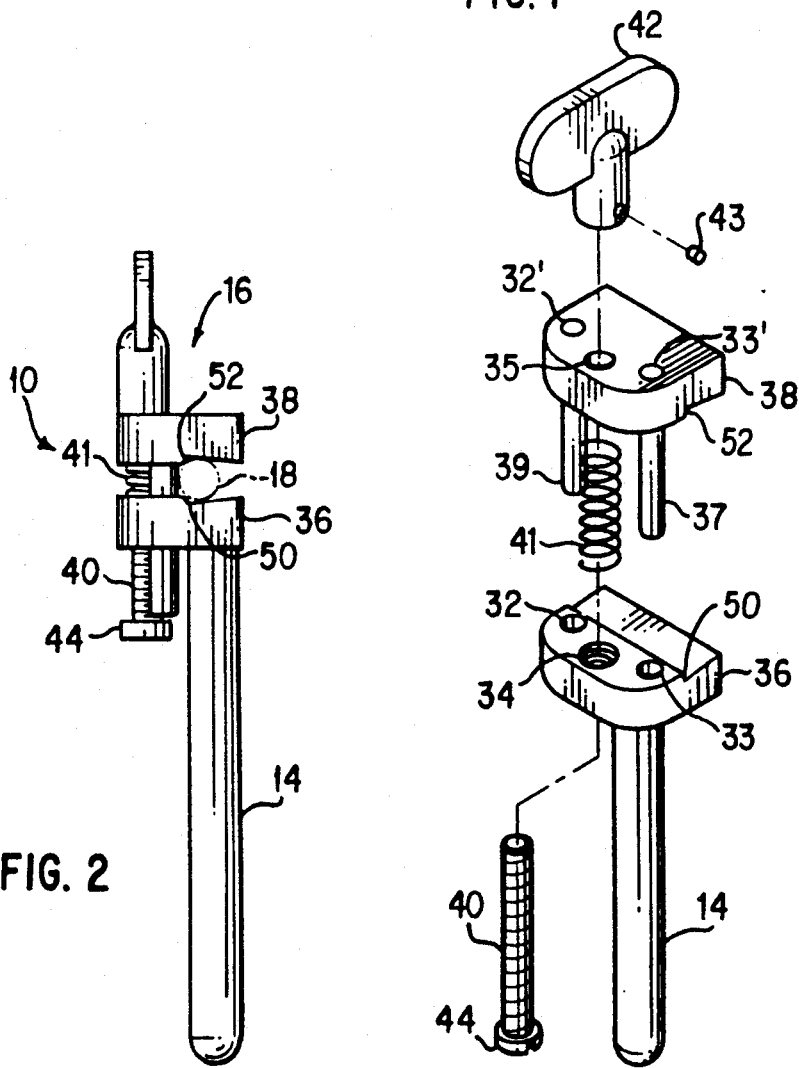
FIG. 2 is a side elevational view of the first embodiment of my surgical instrument holder of the present invention.
Figure 3:
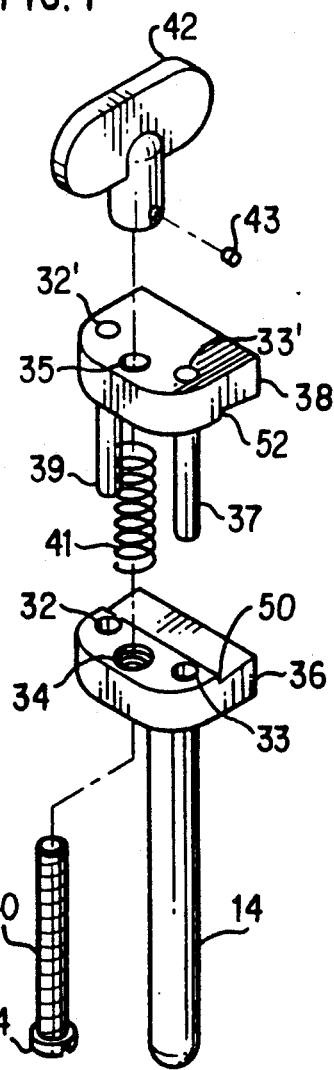
FIG. 3 is an exploded perspective view of the surgical instrument holder of FIGS. 1 and 2.

With reference to FIGS. 2 and 3, clamp assembly 16 comprises a pair of movable jaws 36,38. Each jaw has three openings or holes formed therein. A lower pair of spaced holes 32,33 are provided in jaw 36 through which a pair of axially aligned guide rods 37,39 are passed. The guide rods 37,39 are fixedly mounted in holes 32',33' in the upper jaw 38 so as to be slidably received in the corresponding lower holes 32,33. Aligned holes 34,35 are also provided in jaws 36,38. A threaded shaft or bolt 40 is positioned in the holes 34,35 to permit activation of the holder. Aligned hole 35 in jaw 38 has a smooth bore whereas aligned hole 34 in jaw 36 is threaded to engage the threaded portion of bolt 40. A T-handle 42 is mounted to bolt 40 and secured thereto by pin 43 to rotate bolt 40 thereby causing jaws 36,38 to open and close with respect to each other.

A coil spring 41 is disposed about bolt 40 intermediate jaws 36,38 so as to bias the jaws for ease in opening the holder and removing the instrument. A boss 44 is provided on the end of shaft 40 opposite T-handle 42 limits the extent to which jaws 36,38 may be opened to at least about 13 mm or more so as to accommodate instruments having differing diameters. Boss 44 also prevents the components of the holder from inadvertently being disconnected.

Figure 4A:
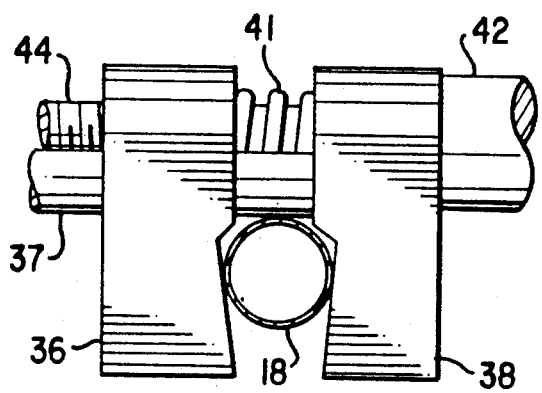
FIG. 4a is an enlarged side sectional view of area A—A of my FIG. 2 embodiment.
Figure 4B:
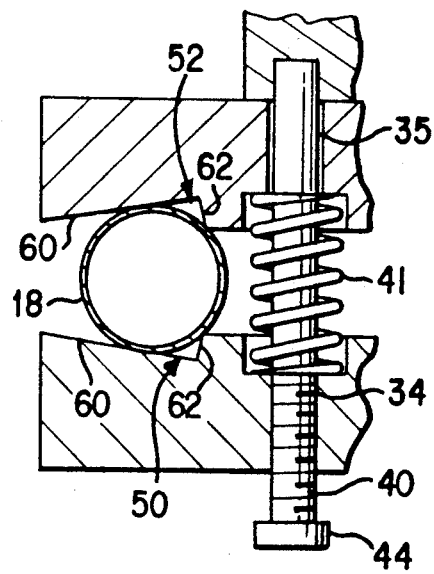

With reference to FIGS. 4a and 4b, the inner face of each jaw is preferably provided with a longitudinal notch 50,52 for receiving and gripping the laparoscope or other instrument. The notches readily receive a surgical instrument having a diameter of between 2.5 and 12 mm. Notches 50,52 extend parallel to the longitudinal axis of the laparoscope 18 to also provide a more even distribution of force about the circumference of the instrument to lessen the deformation and bending thereof. Longitudinal notches 50,52 are formed of a pair of inclined surfaces 60,62 directed inwardly towards each other such that the angle there-between is approximately 90°. It is also preferable that inclined surfaces 60 be significantly longer than inclined surfaces 62.

With reference to FIG. 4a, when an instrument of suitable diameter is inserted into the device, guide rods 37,39 function to further stabalize the instrument as shown. Allowing instrument 18 to abut guide rods 37,39 creates five separate points of contact between the instrument and the device thereby lessening the liklihood of deformation.

In addition to the longitudinal notch, other notch configurations can be utilized, such as, a curved indentation having a hemispherical cross-section. Irrespective of the notch shape, the surface is smooth so as not to mar the instrument being secured.

Another feature of the first embodiment of the present invention is that the longitudinal notches 50,52 are spaced a sufficient distance from holes 32,33 and 34,35, such that, when the instrument 18 is held by the jaws it will avoid touching the spring 41. It has been found that the operability of some sensitive medical instruments has been interfered with when the spring is permitted to contact the instrument.

Figure 5A:
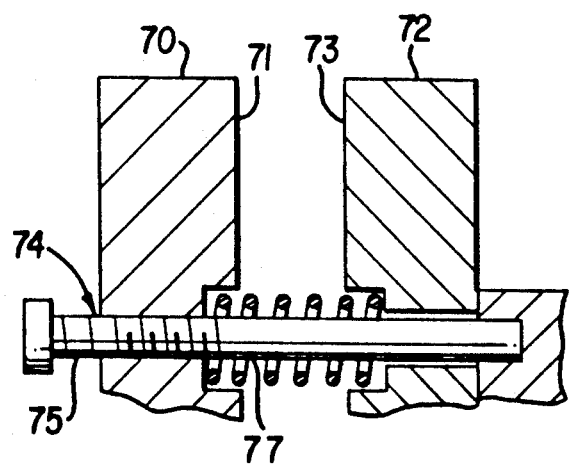
FIG. 5a is an enlarged sectional view of a second embodiment of my surgical instrument holder, shown in the same region as is FIG. 2 with respect to my first embodiment.
Figure 5B:
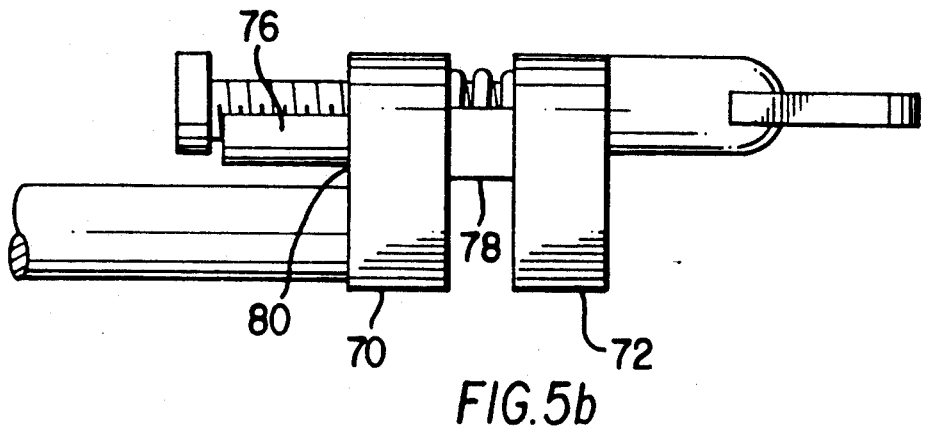
Figure 6:
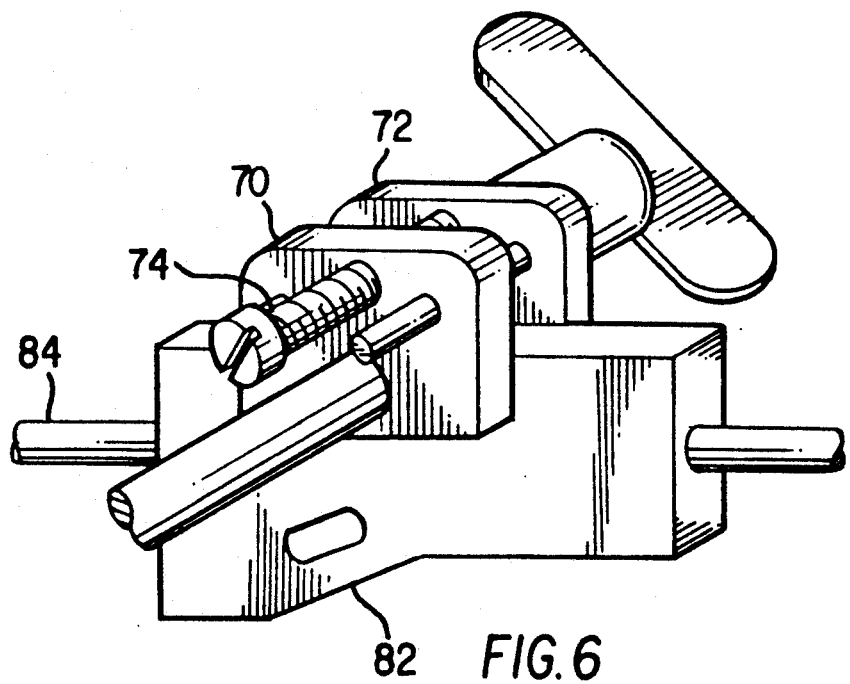
FIG. 6 is a perspective view of the second embodiment of my surgical instrument holder shown gripping the head portion of a disposable plastic trocar.

The second embodiment of the present invention, illustrated in FIGS. 5a, 5b and 6, is designed to grip the head portion 82 of a disposable trocar, such as that commercially sold under the trademark SURGIPORT ®, and described in U.S. Pat. No. 4,654,030 to Moll et al or others sold by the Ethicon Corporation. Disposable trocars have cannulae 84 constructed of radioluscent plastic which will easily collapse and bend from the clamping force. It is therefore desirable to support the trocar by gripping the rigid, rectangular trocar head 82. Thus, jaws 70,72 are provided with planar surfaces 71,73 which are roughened on the respective confrontilg faces of jaws 70,72 to securely grip the rectangular trocar head 82. It is necessary to provide rough surfaces only on the portion of the confronting face of jaws 70,72 which is in contact with the instrument. Since the trocar head 82 is about 12.5 to 27 mm wide, a larger bolt 74 is provided to permit a wide opening of the jaws 72,74 to receive head 82. Naturally, the length of the bolt 74 can be varied depending on the width or thickness of the instrument being secured.

To prevent the holder of the second embodiment from being inadvertently applied to a laparoscope, metal trocar cannula, or other fragile instrument, bolt 74 is comprised of a threaded portion 75 and an unthreaded portion 77 such that further tightening is prevented when jaw 70 abuts the unthreaded portion 77 (FIG. 5a). Threaded portion 75 is of a length such that jaws 70,72 are prevented from closing closer than 12.5 mm which effectively prevents application of the second embodiment on laparoscopes and the like—which rarely have diameters exceeding 12 mm—so as to prevent damage to the expensive instrument. This contrasts with the first embodiment which utlizes a constant diameter rod thereby allowing the jaws to be closed fully or partially, depending on the nature of the use.

Alternatively, and with reference to FIG. 5b guide rods 76 of the second embodiment may include an expanded portion 78 having a diameter larger than that of the adjacent portion which passes through the holes 80, such that further tightening is prevented when the jaw 70 abuts the expanded portion 78.

In use, the operating room table clamping apparatus 26, preferably the IRON INTERN ® device disclosed in the Meir et al patent, is mounted to the operating room table. Arm 14 of instrument holder 10 is inserted into socket 30 of the IRON INTERN ® and is locked therein by tightening handle 31. As more completely described by Meir et al, the subject matter of which is incorporated herein by reference, the plurality of interconnecting hinges and ball joints provided with table stand 28 (not completely shown) allows a full range of movement of holder 10. Holder 10 is positioned such that the jaws are adjacent the laparoscope 18 which has been inserted into the abdomen of the patient. The jaws are opened, laparoscope 18 or trocar cannula 20 is passed therebetween and the jaws are tightened accordingly. It is a particular feature of the present invention that holder 10 need not be positioned on the laparoscope or other instrument prior to the instrument being inserted into the body of the patient thereby allowing the instrument to be positioned with ease prior to applying mechanical fixation.

The second embodiment of the present invention is used substantially the same as the first embodiment except that jaws 70,72 are made to pass over trocar head 82.

Although certain presently preferred embodiments of the invention have been described herein, it will be apparent to those skilled in the art to which the invention pertains that variations and modifications of the described embodiment may be made without departing from the spirit and scope of the invention. Accordingly, it is intended that the invention be limited only to the extent required by the appended claims and the applicable rules of law.

What is claimed is:

1. A surgical instrument holder, adapted to removably retain one of a multiplicity of instruments for laparoscopic surgery;
    said surgical instruments comprising elongated thin-wall tubular shafts, or various diameters;
    said holder comprising a pair of moveable jaws for gripping said thin-wall tubular shaft, without deforming the walls thereof, the inner face of at least one of said jaws including an indentation for receiving and securely retaining said thin-walled tubular shafts of various diameters;
    a bolt rotatably positioned through said moveable jaws;
    a handle operatively secured to one end of said bolt for moving said jaws;
    an attachment member mounted to said holder for removably securing said holder to an operating room table supporting apparatus;
    whereby said surgical instrument may be stably positioned during laparoscopic surgery without support from humans.

2. The surgical instrument holder of claim 1, further including a spring for urging said jaws apart.

3. The surgical instrument holder of claim 2, further including guide means for opening and closing said jaws, said guide means comprising at least one rod which projects from one of said jaws, and a corresponding opening in said opposite jaw for slidably receiving said rod therein.

4. The surgical instrument holder of claim 1, wherein both jaws include an indentation in the confronting faces.

5. The surgical instrument holder of claim 4, wherein said indentations are identical notches.

6. The surgical instrument holder of claim 5, wherein each of said notches forms an obtuse angle at its apex.

7. The surgical instrument holder of claim 6, further including guide means for opening and closing said jaws, said guide means comprising at least one rod which projects from one of said jaws, and a corresponding opening in said opposite jaw for slidably receiving said rod therein.

8. The surgical instrument holder of claim 5, wherein each of said notches comprises a first inclined surface and a second inclined surface substantially smaller than said first inclined surface.

9. The surgical instrument holder of claim 8, wherein said means for cooperating with said operating room table clamping apparatus comprise an elongated arm secured to one of said jaws, substantially perpendicular to the longitudinal axis of said instrument being gripped by said holder.

10. The surgical instrument holder of claim 4, further including guide means for opening and closing said jaws, said guide means comprising at least one rod which projects from one of said jaws, and a corresponding opening in said opposite jaw for slidably receiving said rod therein.

11. The surgical instrument holder of claim 1, wherein said indentation is a notch.

12. The surgical instrument holder of claim 11, wherein said notch forms an approximately right angle at its apex.

13. The surgical instrument holder of claim 11, wherein said notch comprises a first inclined surface and a second inclined surface substantially smaller than said first inclined surface.

14. The surgical instrument holder of claim 1, wherein said spring is an elongated coil spring having an opening sufficiently large to receive said bolt; said opening in each jaw through which said bolt passes being recessed to receive the opposite ends of said coil spring.

15. The surgical instrument holder of claim 14, wherein one of said jaw openings is internally threaded to engage corresponding threads on said bolt.

16. The surgical instrument holder of claim 14, wherein the inner face of one of said jaws defines an indentation for receiving and retaining the shaft of said instrument.

17. The surgical instrument holder of claim 16, wherein inner face of one of said jaws is roughened.

18. The surgical instrument holder of claim 16, wherein said indentation is a notch.

19. The surgical instrument holder of claim 16, wherein said indentation is curved.

20. The surgical instrument holder of claim 14, wherein both jaws include an indentation in the confronting faces.

21. The surgical instrument holder of claim 20, wherein both jaws include an indentation in their confronting faces which are identical.

22. The surgical instrument holder of claim 20, wherein each of said indentations is curved.

23. The surgical instrument holder of claim 14, wherein both jaws include roughened confronting faces.

24. The surgical instrument holder of claim 14, further including guide means for opening and closing said jaws, said guide means comprising at least one rod which projects from one of said jaws, and a corresponding opening in said opposite jaw for slidably receiving said rod therein.

25. The surgical instrument holder of claim 14, wherein said means for cooperating with said operating room table clamping apparatus comprise an elongated arm secured to one of said jaws, substantially perpendicular to the longitudinal axis of said instrument being gripped by said holder.

26. The surgical instrument holder of claim 1, further including guide means for opening and closing said jaws, said guide means comprising at least one rod which projects from one of said jaws, and a corresponding opening in said opposite jaw for slidably receiving said rod therein.

27. The surgical instrument holder of claim 26, wherein said means for cooperating with said operating room table clamping apparatus comprise an elongated arm secured to one of said jaws, substantially perpendicular to the longitudinal axis of said instrument being gripped by said holder.

28. The surgical instrument holder of claim 1, further including guide means for opening and closing said jaws, said guide means comprising at least one rod which projects from one of said jaws, and a corresponding opening in said opposite jaw for slidably receiving said rod therein.

29. The surgical instrument holder of claim 1, further including guide means for opening and closing said jaws, said guide means comprising at least one rod which projects from one of said jaws, and a corresponding opening in said opposite jaw for slidably receiving said rod therein.

30. The surgical instrument holder of claim 1, wherein said means for cooperating with said operating room table clamping apparatus comprise an elongated arm secured to one of said jaws, substantially perpendicular to the longitudinal axis of said instrument being gripped by said holder.

31. A holder for a disposable trocar adapted to removably retain the head of the disposable trocar which is generally made of plastic, said holder comprising:
   a pair of moveable jaws for security gripping said trocar head, the inner face of at least one of said jaws including a plurality of serrations;
   a bolt rotatably positioned through said movable jaws for moving said jaws;
   means for preventing said jaws from closing beyond a predetermined distance to prevent said holder from being inadvertently applied to non-disposable laparoscopic instruments and thereby damaging said non-disposable instruments;
   an attachment member, mounted to said holder, adapted to attach the holder to an operating room table supporting apparatus;
   whereby said trocar may be stably positioned during laparoscopic surgery without support from humans.

32. The surgical instrument holder of claim 31 wherein said at least one rod has a first portion and a second portion opposite said first portion, said second portion having a diameter larger than the diameter of said opening in said opposite jaw, to prevent said jaws from closing beyond a predetermined distance.

33. The surgical instrument holder of claim 31 wherein said means for preventing said jaws from closing beyond a determined distance comprises guide means which includes at least one rod having a first portion and a second portion opposite said first portion, said second portion having a diameter larger than the diameter of said opening in said opposite jaws.

34. The surgical instrument holder of claim 31, wherein said bolt has a first portion that is threaded and a second portion that is unthreaded opposite said first portion to prevent said jaws from closing beyond a predetermined distance.

* * * * *